US008734332B2

(12) United States Patent
Krattiger et al.

(10) Patent No.: US 8,734,332 B2
(45) Date of Patent: May 27, 2014

(54) CONNECTOR UNIT FOR ENDOSCOPES

(75) Inventors: Beat Krattiger, Beringen (CH); Martin Klumpp, Tuttlingen (DE); Manfred Kuster, Widnau (CH)

(73) Assignee: Storz Endoskop Produktions GmbH (DE)

( * ) Notice: Subject to any disclaimer, the term of this patent is extended or adjusted under 35 U.S.C. 154(b) by 1225 days.

(21) Appl. No.: 11/676,041

(22) Filed: Feb. 16, 2007

(65) Prior Publication Data

US 2008/0009672 A1 Jan. 10, 2008

Related U.S. Application Data

(63) Continuation of application No. PCT/EP2005/008664, filed on Aug. 10, 2005.

(30) Foreign Application Priority Data

Aug. 19, 2004 (DE) ............... 20 2004 012 991 U

(51) Int. Cl.
  *A61B 1/04* (2006.01)
(52) U.S. Cl.
  USPC ............ 600/132; 600/102; 600/104; 600/112
(58) Field of Classification Search
  USPC ......... 600/112, 132, 104, 106–107, 153–154, 600/159
  See application file for complete search history.

(56) References Cited

U.S. PATENT DOCUMENTS

| 4,261,345 A | | 4/1981 | Yamaguchi ................. 128/6 |
| 4,402,313 A | * | 9/1983 | Yabe ............... 600/132 |
| 4,527,551 A | | 7/1985 | Ishii ................... 128/4 |
| 4,667,655 A | | 5/1987 | Ogiu et al. |
| 4,754,328 A | * | 6/1988 | Barath et al. .................. 348/67 |
| 4,984,563 A | * | 1/1991 | Renaud ................ 600/108 |
| 5,239,983 A | * | 8/1993 | Katsurada ................ 600/178 |
| 5,460,168 A | * | 10/1995 | Masubuchi et al. ............ 600/123 |
| 5,536,235 A | * | 7/1996 | Yabe et al. ................ 600/121 |
| 5,643,175 A | * | 7/1997 | Adair ............... 600/133 |
| 5,879,288 A | * | 3/1999 | Suzuki et al. ................ 600/176 |
| 6,234,958 B1 | * | 5/2001 | Snoke et al. ................ 600/114 |
| 6,432,041 B1 | * | 8/2002 | Taniguchi et al. ............ 600/118 |
| 6,443,888 B1 | | 9/2002 | Ogura et al. |

(Continued)

FOREIGN PATENT DOCUMENTS

DE 103 21 444 12/2003
EP 0 726 059 A1 8/1996

OTHER PUBLICATIONS

International Search Report, Dec. 8, 2005, 2 pages.
German Search Report, Mar. 8, 2005, 2 pages.

(Continued)

*Primary Examiner* — Matthew J Kasztejna
(74) *Attorney, Agent, or Firm* — St. Onge Steward Johnston & Reens LLC

(57) ABSTRACT

A plug-in unit with integral cable connection to the operating part of an endoscope and plug connections for lamps, mechanical, and/or electronic modules is characterized in that a hollow tube extending to the distal end of the endoscope is inserted into the plug-in unit by the integral cable connection and the operating part and has its proximal end positioned so that it is freely movable in the plug-in unit in such a way that can be conducted out of a closeable bore-hole in the wall of the plug-in unit.

5 Claims, 3 Drawing Sheets

(56) References Cited

U.S. PATENT DOCUMENTS

| | | | |
|---|---|---|---|
| 6,520,954 B2* | 2/2003 | Ouchi | 606/1 |
| 6,569,087 B2* | 5/2003 | Naito et al. | 600/156 |
| 6,679,835 B2* | 1/2004 | Moriyama | 600/133 |
| 2001/0025135 A1* | 9/2001 | Naito et al. | 600/156 |
| 2002/0040181 A1 | 4/2002 | Arai et al. | |
| 2003/0220545 A1 | 11/2003 | Ouchi | |
| 2004/0171913 A1* | 9/2004 | Saruya | 600/132 |
| 2005/0113641 A1* | 5/2005 | Bala | 600/108 |
| 2006/0052663 A1* | 3/2006 | Koitabashi | 600/132 |
| 2009/0259100 A1* | 10/2009 | Ito et al. | 600/110 |

OTHER PUBLICATIONS

International Preliminary Report on Patentability, Feb. 20, 2007, 7 pages.

\* cited by examiner

CONNECTOR UNIT FOR ENDOSCOPES

CROSS-REFERENCE TO RELATED APPLICATIONS

The present application is a continuation of pending International patent application PCT/EP2005/008664 filed on Aug. 10, 2005 which designates the United States and claims priority from German patent application 20 2004 012991.4 filed on Aug. 19, 2004, the content of which is incorporated herein by reference.

FIELD OF THE INVENTION

The invention relates to a plug-in unit with integral cable connection to the operating part of an endoscope and plug connections for lamps, mechanical, and/or electronic modules.

BACKGROUND OF THE INVENTION

Endoscopes, in particular those for industrial measurement and inspection tasks, usually contain a number of peripheral devices for power supply, lighting, video camera control, image evaluation, monitors, and the like. To avoid unnecessary obstacles to the handling of the endoscope with its operating part, a plug-in unit is provided from which the optical and electronic supply, as well as data exchange, is conducted to the endoscope by way of an integral cable connection. The number of plug connections corresponds to the number of possible peripheral devices for the particular endoscope, so that the plug-in unit allows essentially a simple exchange of various peripheral devices of the same type. The plug-in unit is configured in such a way that the mechanical impact of the integral cable connection upon connecting the peripheral devices is as small as possible.

It is the object of the invention to refine the plug-in unit in such a way that newly developed additional modules, or those not foreseen at first for the particular endoscope, can be retrofitted without rebuilding or disassembling the other plug connections. It should be possible in this case to connect the module with the plug-in unit in such a way that the static-mechanical impact of the integral cable connection is not unfavorably influenced.

SUMMARY OF THE INVENTION

This object is fulfilled in that a hollow tube running up to the distal end of the endoscope is inserted into the plug-in unit by the integral cable connection and the operating part, and its proximal end is positioned so that it is freely movable in the plug-in unit so that it can be conducted out of a closable bore-hole in the wall of the plug-in unit. A hollow axle for inserting the hollow tube can be inserted into the open bore-hole. An additional module can be mounted on the hollow axle in such a way that the functionally determining part of the additional module is linked to the proximal aperture of the hollow tube. The housing of the additional module here is most usefully configured in a shaping mold that surrounds the plug-in unit and has its center of gravity on the axis of the integral cable connection. A single-mode laser fiber, with a collimation lens connected to it on the distal side and a laser diode mounted upstream in the housing on the proximal side, can be inserted into the hollow tube.

One embodiment of the invention is depicted schematically in the illustrations.

BRIEF DESCRIPTION OF THE DRAWINGS

FIG. 1a shows a close-up, cross-section view of the distal end of the endoscope of FIG. 1.

DETAILED DESCRIPTION OF THE INVENTION

Figure 1:
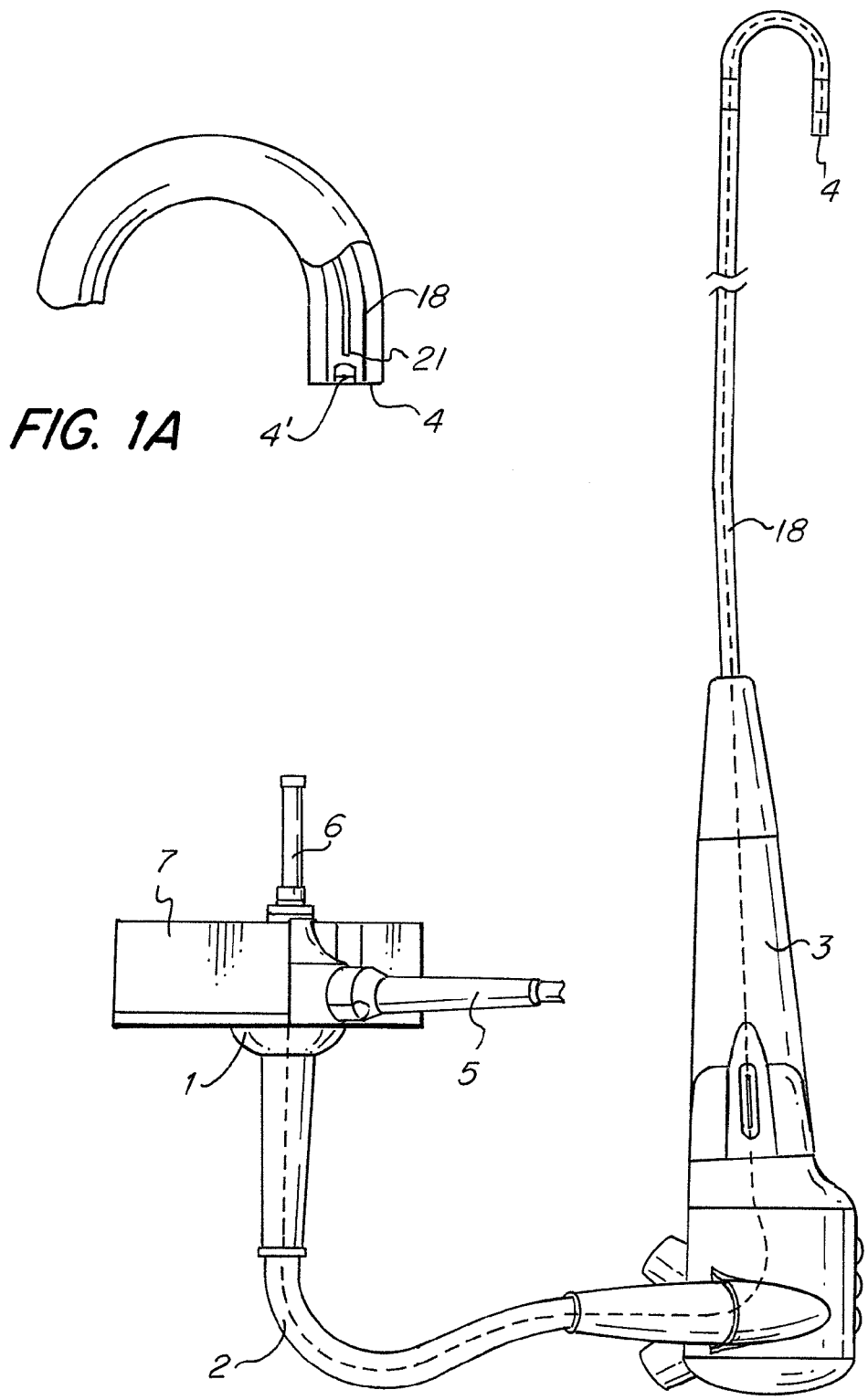
FIG. 1 shows an overall view of an endoscope including plug-in unit, integral cable connection, and operating part.

A plug-in unit 1 depicted in FIG. 1 is connected by an integral cable connection 2 with the operating part 3 of an endoscope. This endoscope can be, for instance, a video measurement endoscope, whose distal end 4 can be moved by means of a Bowden cable. The measurement endoscope can also be a multi-point or a two-point measuring system, which is supplied by means of a plug-in unit 1.

The plug-in unit 1 includes two plug connections 5, 6. The plug connection 5 contains, for instance, the lines to the video camera control and image evaluation, and a lighting unit, for instance, can be mounted on the plug connection 6. Additional plug connections, for instance for power supply, are not shown in further detail here.

A housing 7 for an additional module is connected to the plug-in unit 1. The housing 7 is configured in such a shape that it surrounds the plug-in unit 1 from the side, in particular so that the plug connection 5 remains free. The housing 7 here is constructed in such a way that its center of gravity lies on the longitudinal axis of the integral cable connection 2 running through the plug-in unit 1. When there is a tug on the plug-in unit 1 because of the operation and motion of the endoscope, the integral cable connection 2 can pick up the forces from there, without additional cross-forces arising. The housing 7 of the additional module thus becomes a component of the plug-in unit 1.

The housing 7 of the additional module can be adapted for various applications, which can be performed on an object area that is to be examined by way of a hollow tube extending from the plug-in unit 1 and leading through the integral cable connection 2 and the operating part 3 to the distal end. The proximal end of the hollow tube is at first positioned so that it is freely movable in the plug-in unit 1 in such a way that it can when necessary be conducted out of a bore-hole in the wall of the plug-in unit 1 that is closed by a plug. To prepare for the starting of the additional module, the bore-hole is opened and a hollow axle is inserted in the wall, into which the proximal end of the hollow tube is then drawn. Depending on the equipping of the additional module, its function-determining part is mounted in the housing 7 in such a way that can interact with the aperture of the hollow tube. The hollow axle here serves to orient and hold the housing 7 on the plug-in unit 1. With the help of an additional adjusting pin, the housing 7 can be secured on the plug-in unit 1 against any rotation.

Figure 3:
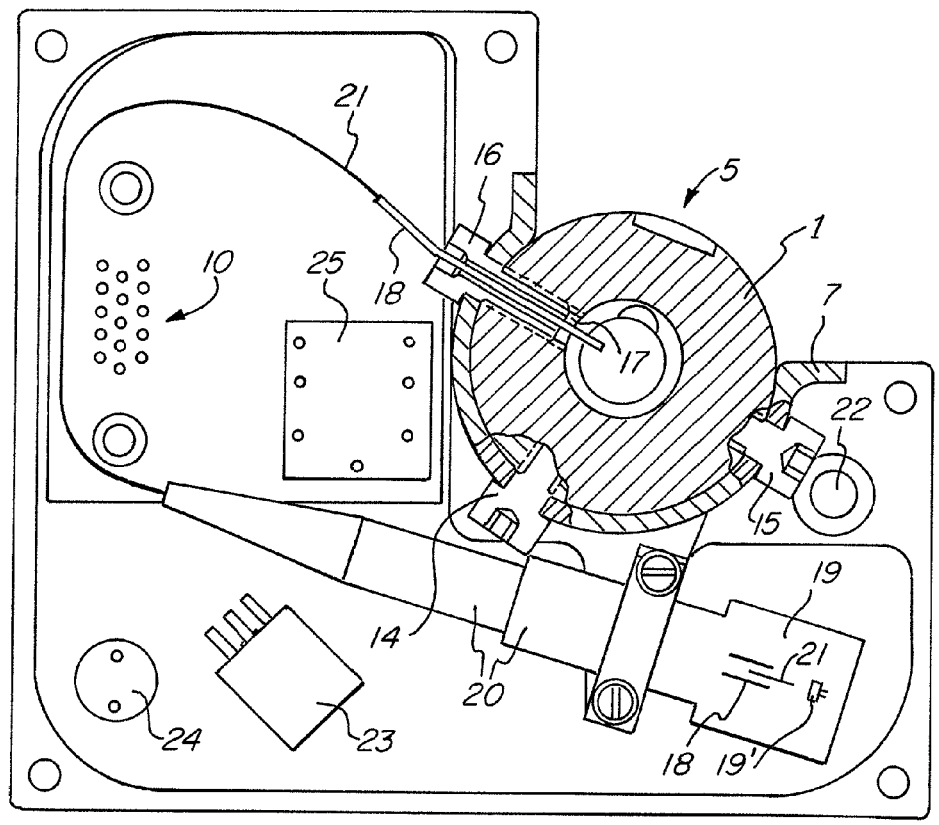
FIG. 3 shows a cross-section through the plug-in unit and the additional module.

An initial additional module can be provided for irradiating laser light onto the object. For this purpose a single-mode laser fiber is inserted into the hollow tube and on the distal side has a collimation lens 4' mounted as shown in FIG. 1a. On the proximal side the housing 7 has as its function-determining part a laser diode 19', whose radiation is coupled into the single-mode laser fiber, as shown in FIG. 3. To supply the laser diode with energy, an appropriate plug-in connection can be provided on the housing 7 for connecting to a supply unit. The retrofitting of the system is advantageously handled by the manufacturer in order to ensure the mutual adjustment of the functional elements. Clearly, no dismantling of the existing connections is necessary.

Figure 2:
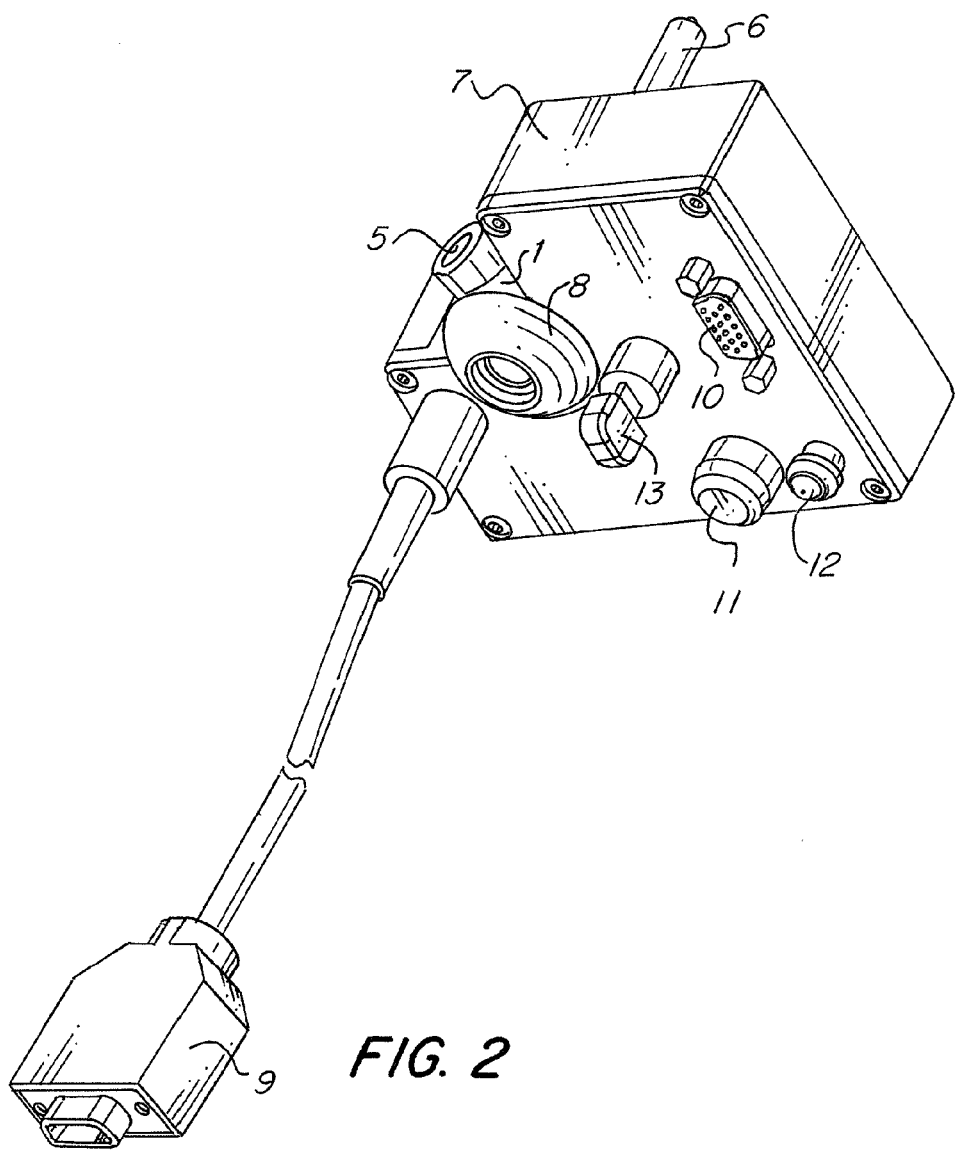
FIG. 2 shows a perspective view of the plug-in unit with the operating side of an additional module.

FIG. 2 shows such an additional module in a perspective view of its operating side. The illustration depicts the spherical-cap-shaped stub 8 of the plug-in unit 1, into which the integral cable connection 2 is inserted. On the plug-in unit 1 the stub for the plug connection 5 for video camera control can be seen in a side view, with the plug connection 6 directed upward for a lighting unit. The housing 7 of the additional module surrounds the plug-in unit 1 from the outside, so that the area of the plug connection 5 remains free. The housing 7 in addition is equipped with a plug-in socket 10 for connecting additional external devices. The lighting intensity can be controlled by a potentiometer rotation knob 11. An indicator lamp 12 serves to indicate the device is in operation. The additional module can be centrally put into operation by a key switch 13.

The cross-sectional view presented in FIG. 3 corresponds to a view from the rear side of the plug-in unit and additional module. On the plug-in unit 1, the housing 7 is moved up in form-locking connection and is connected with the plug-in unit 1, secure against rotation, by way of at least one adjuster pin 14, 15 configured as a bolt. The orientation of the plug-in unit 1 and the housing 7 to one another is selected in such a way that a hollow axle 16 inserted into the wall of the housing 7 is flush with a bore-hole 17 in the plug-in unit. A hollow tube 18 is conducted from the integral cable connection (not further depicted here) into the housing 7 through the bore-hole 17 and the hollow axle 16.

Inside the housing 7 a laser diode is positioned in a frame 19. The frame 19 contains an optical plug-in connection 20 for connecting a laser fiber 21, which is inserted into the hollow tube 18.

A laser diode radiating in the visible wavelength range can be provided as a laser light source. Preferably the laser diode should operate at 639 nm (3 nm. The dissoluble plug-in device 20 serves to couple the single-mode laser fiber to the laser diode, Repairs are facilitated by the dissoluble connection, and the allocation of the single-mode laser fiber to the insert surface is ensured.

The laser diode to be used and/or the laser diode drive should be arranged so that speckles in the radiation field are reduced. For this purpose, speckles-reducing materials can be positioned between the laser diode and the insert surface of the single-mode laser fibers. The visibility of the measurement pattern on the object is clearly improved by suppressing speckles.

Also visible in the sectional view are the passageway aperture 22 for the energy supply lines connected with the plug connection 9, a potentiometer 23 that can be displaced with the rotation knob, a lamp socket 24 for the indicator lamp 12, and a switching plate 25 for the key switch 13.

Further examples of equipment for additional modules include grinding devices, sensors, manipulation devices, other additional illumination, spraying, arranging or dosing devices, whose use can be triggered on the housing 7 by actuation elements and control means conducted through the hollow tube.

What is claimed is:

1. A plug-in unit for an integral cable connection to the operating part of an endoscope, comprising:
   at least one plug connection for a lighting and/or electronic module;
   a closeable borehole formed in a wall of the plug-in unit, wherein the borehole is substantially orthogonal to the longitudinal axis of the integral cable connection in the plug-in unit;
   a hollow axle at least partially disposed in the borehole; and
   a hollow tube movably disposed in the plug-in unit and comprising a first portion that extends through the borehole via the hollow axle to the outside of the plug-in unit and a second portion that extends through the integral cable connection and the operating part of the endoscope to the distal end of the endoscope.

2. The plug-in unit according to claim 1, wherein the hollow axle is mounted in a housing of an additional module and holds the housing of the additional module on the plug-in unit such that the first portion of the hollow tube extends into the housing of the additional module.

3. A plug-in unit according to claim 2, wherein a proximal end of the first portion of the hollow tube is associated with a function-determining part of the additional module.

4. A plug-in unit according to claim 3, wherein the housing of the additional module at least partially surrounds the plug-in unit and has a center of gravity that lies on the axis of the integral cable connection.

5. A plug-in unit according to claim 3, wherein a single-mode laser fiber is inserted into the hollow tube, wherein said single-mode laser fiber has a collimation lens connected to it on its distal side and said single-mode laser fiber has a laser diode upstream from it on its proximal side, and said single-mode laser fiber is positioned in a frame in the housing of the additional module.

* * * * *